(12) United States Patent
Grossmann et al.

(10) Patent No.: US 6,486,666 B1
(45) Date of Patent: Nov. 26, 2002

(54) METHOD AND APPARATUS FOR MEASURING THE DEGREE OF POLARIZATION OF POLARIZED GAS

(75) Inventors: Tino Grossmann, Mainz (DE); Werner Heil, Varces Alliers et Risset (FR); Daniela Rohe, Koblenz (DE); Reinhard Surkau, Mainz (DE); Elke Aidam, Wörth (DE); Michael Ebert, Wörrstadt (DE); Ernst-Wilhelm Otten, Mainz (DE)

(73) Assignee: Hellspin Polarisierte Gase GmbH, Mainz (DE)

(*) Notice: Subject to any disclaimer, the term of this patent is extended or adjusted under 35 U.S.C. 154(b) by 0 days.

(21) Appl. No.: 09/509,229

(22) PCT Filed: Sep. 24, 1998

(86) PCT No.: PCT/EP98/06055

§ 371 (c)(1),
(2), (4) Date: May 18, 2000

(87) PCT Pub. No.: WO99/17105

PCT Pub. Date: Apr. 8, 1999

(30) Foreign Application Priority Data

Sep. 26, 1997 (DE) .......................... 197 42 543

(51) Int. Cl.[7] .................................................. G01V 3/00
(52) U.S. Cl. ........................................ 324/300; 62/637
(58) Field of Search ............................... 324/300, 301, 324/302, 303, 304, 305, 321; 62/637; 250/251

(56) References Cited

U.S. PATENT DOCUMENTS 4,617,462 A * 10/1986 Holt ........................... 250/251
5,122,746 A * 6/1992 King et al. .................. 324/307
6,295,834 B1 * 10/2001 Driehuys ...................... 62/637

OTHER PUBLICATIONS

Noel E et al: "Measurement of the Nuclear Polarisation of Optically Pumped He Atom Using a He Magnetometer", Journal de Physique III, vol. 6, No. 8, Aug. 1, 1996, pp. 1127–1132, XP000621593 –See the whole document.

Cohen–Tannoudji C et al: "Detection of the Static Magnetic Field Produced by the Oriented Nuclei of Optionally Pumped He Gas", Physical Review Letters, Apr. 14, 1969, USA, vol. 22, No. 15, pp. 758–760, XP002092581, ISSN 0031–9007, See the whole document.

Lorenzon W et al: "NMR Calibration of Optical Measurement of Nuclear Polarization in He", Physical Review A (Atomic, Molecular, and Optical Physics), Jan. 1993, USA, vol. 47, No. 1, pp. 468–479, XP002092582, ISSN 1050–2947, Chapter II.A.

Wilms E et al: "Polarimetry on Dense Samples of Spin–Polarized He by Magnetostatic Detection", Nuclear Instruments & Methods in Physics Research, Section A (Accelerators, Spectrometers, Detectors and Associated Equipment), Dec. 21, 1997, Elsevier, vol. 401, No. 2–3, pp. 491–498, XP002092583, ISSN 0168–9002, See the whole document.

* cited by examiner

Primary Examiner—Louis Arana

(57) ABSTRACT

The invention relates to a method for determining the degree of polarization (P) of a nuclear spin polarized gas, in particular $^3$He, $^{129}$Xe, in which the nuclear spin polarized gas is placed in a container, comprising determining the magnetic field $B_d$ of the pola gas by measuring the magnetic dipole field emerging therefrom and then determining from $B_d$ the degree of polarization of the gas.

26 Claims, 3 Drawing Sheets

METHOD AND APPARATUS FOR MEASURING THE DEGREE OF POLARIZATION OF POLARIZED GAS

METHOD AND APPARATUS

Figure 1:
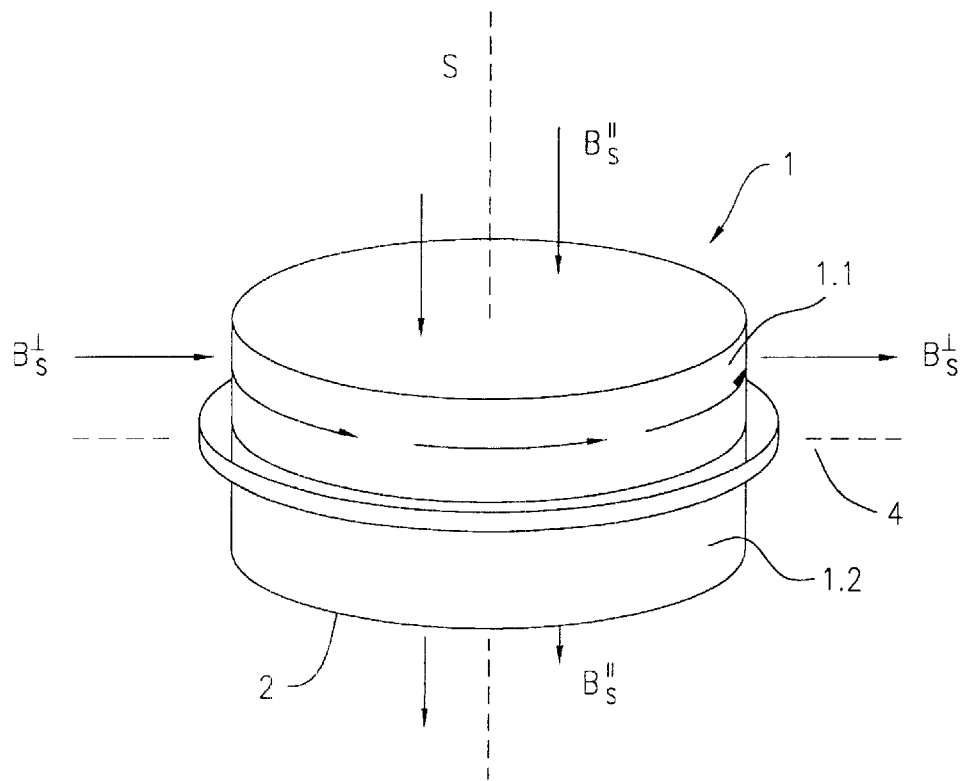

The invention relates to a method and apparatus for determining the degree of polarisation of nuclear spin polarised gases, in particular 3He or $^{129}$Xe.

Nuclear spin polarised gases, such as the helium isotope with mass number 3 ($^3$He) or the isotope of xenon with mass number 129 ($^{129}$Xe) and gases containing the fluorine, carbon or phosphorus isotopes $^{19}$F, $^{13}$C or $^{31}$P, are required for a wide variety of basic physics research experiments.

In the medical field, such isotopes have particularly been discussed for use in nuclear spin tomography (magnetic resonance imaging), for example of the lung. (See for example WO95/27438, WO97/37239, Bachert et al., Mag. Res. Med. 36: 192–196 (1996) and Ebert et al., The Lancet 347: 1297–1299 (1996)). In addition, Noël et al., J. Phys. III France 6: 1127–1132 (1996) discloses a $^4$He magnetometer used to detect the static magnetic field produced by optically pumped $^3$He nuclei submitted to RF discharge. Similarly, Cohen-Tannoudji et al., Phys. Rev. Letts. 22: 758–760 (1969) discloses the use of a sensitive low-field magnetometer to detect the static magnetic field produced by optically pumped $^3$He nuclei in a vapor. To be useful in nuclear spin tomography, the nuclear spin polarised gases require a degree of polarisation P of spin I of the atomic nucleus, or the nuclear magnetic dipole moment $\mu_I$ connected therewith, which is about 4–5 orders of magnitude larger than $P_{Boltzman}$ the degree of polarisation of the gas in its relaxed state in normal thermal equilibrium in the magnetic field $B_T$ of the mr imaging apparatus. $P_{Boltzmann}$ is related to the Boltzmann constant, the magnetic dipole energy $-\mu_I B_T$ and thermal energy kT by:

$$P_{Boltzmann} = \tan h(\mu_I B_T / kT) \quad (1)$$

(where k=Boltzmann constant, and T=absolute temperature in Kelvin).

Where $P_{Boltzmann} \ll 1$, then it approximates to $\mu_I B_T/kT$.

Since routinely $B_T=1.5T$ and $T=300K$ for the hydrogen isotope $^1$H used in tissue tomography, it has a $P_{Boltzmann}$ of only $5 \times 10^{-6}$, but in gas tomography a $P>1\times 10^{-2}$ (i.e. 1%) is required. The requirement for such an extremely high P is mainly due to the low concentration of gas atoms in comparison to that of hydrogen in tissue. Gases with such degrees of polarisation (normally referred to as "hyperpolarised gases") can be prepared using various known methods, advantageously by optical pumping or by polarization transfer.

In addition, large amounts of hyperpolarised gas, for example of the size of an intake of breath (0.5 to 1 litre) must be prepared for use.

Particularly high degrees of polarisation—for example >30%—in simultaneously high production amounts, for example 0.5 liters/h, may be achieved by compression of an optically pumped gas. This method is described in the following publications:

Eckert et al., Nuclear Instruments and Methods in Physics Research A 320: 53–65 (1992);

Becker et al., J. Neutron Research 5: 1–10 (1996);

Surkau et al., Nuclear Instruments and Methods in Physics Research A 384: 444–450 (1997); and Heil et al., Physics Letters A 201: 337–343 (1995).

The extremely costly production of hyperpolarised gases, for example using the methods described above, generally involves production at a site remote from the place of use. As a result, they must be transported from the place of production to the user. Since a wide variety of relaxation processes (e.g. wall relaxation, relaxation in inhomogeneous, external, stray magnetic fields, etc.) causes the gas to depolarise to a greater or lesser extent, it is necessary to determine the degree of polarisation before using the hyperpolarised gas, for example in medical imaging.

One problem is that this must be determined as precisely as possible despite stray fields or applied fields. Further, the determination should be performable by relatively inexperienced personnel, ie. personnel who are not experts in the physics of hyperpolarized gases.

The present invention solves the above problem by providing a method for determining the degree of polarisation of nuclear spin polarised gases by exploiting the fact that nuclear spin polarisation of gases produces magnetic fields $B_d$ in the nanoTesla to microTesla (nT to $\mu$T) range.

Thus viewed from one aspect the invention provides a method of determining the degree of polarisation (P) of a nuclear spin polarised gas in a container, said method comprising determining the magnetic field $B_d$ of the polarised gas using a magnetic field sensor and then determining therefrom the degree of polarisation of the gas.

In the method of the invention, the shape and size of the container into which the polarised gas is placed is important. Thus, the magnetic field $B_d$, which is dependent on the degree of polarisation of the gases, may be determined using a magnetic field sensor, e.g. a magnetometer, rather than a nuclear magnetic resonance polarimeter as has been used in the past, and the absolute degree of polarisation can be determined from $B_d$ by taking into consideration the geometric shape of the container in which the gas is placed, the type of gas and its density, and the arrangement of the sensor relative thereto.

If, as is preferred, the container in which the gas is received is spherical in shape, then the magnetic field has a field gradient like that formed by a point dipole.

Thus for a spherical container, the magnetic field $B_d$ of the polarised gas on the equitorial outer surface of the container deriving from the orientated nuclear magnetic dipole moment of the nuclear spin gas is:

$$B_d = -P \cdot n \cdot \frac{R^3 \mu_0}{3r^3} \cdot \mu_N \quad (2)$$

where P represents the degree of polarisation to be determined and n the particle density of the gas. The factor $R^3/3r^3$ is termed the geometry factor, and depends on the shape of the container and thus on the volume in which the nuclear spin polarised gas is dispersed. R represents the radius of the sphere and r the distance of the sensor from the centre point of the container sphere perpendicular to the dipole axis. $\mu_0 = 1.257 \times 10^{-6}$ Vs/Am, i.e. the permeability of vacuum, and $\mu_N = 1.075 \times 10^{-26}$ Am$^2$, the nuclear dipole moment of the gas (in this case $^3$He)

Similar equations to equation (2) may be generated for containers which are non-spherical.

The geometric factor also takes the position of the magnetic field measuring apparatus relative to the direction of the magnetic field of the gas into consideration. If the field emerges from the poles of the container, the sensor is positioned in the equatorial plane of the spherical gas container.

Different geometric factors must be used for different container geometries, as in each case there is a different calculable field gradient of magnetic field $B_d$. If the geometric factor, the distance from the measuring sensor and the particle density of the-nuclear spin polarised gas in the container are known, then equation (2) can be used to determine the absolute degree of polarisation P from the $B_d$ determined using the measuring apparatus.

As an example, assuming a degree of polarisation P=50% and a particle density $n=10^{20}/cm^3$, then the field at the edge of the sphere (r=R) has a value $B_d=0.22 \mu T$. This value is of the order of 1 thousandth of the homogeneous magnetic field caused by the polarisation, similar to, for example, transport fields of 0.3 mT, for example, or external stray fields.

In a preferred implementation of the invention, it is proposed that the sensor comprises a very sensitive magnetic field sensor. In this respect, SQUIDs or more preferably sensors operating on the Förster principle can be considered. Förster sensors operate on the principle of saturable-core magnetometers. The measuring element of saturable-core magnetometers essentially consist of one or more narrow cores of highly permeable materials ($\mu$-metal or ferrite) with almost linear B(H) behaviour.

In a variation of a saturable-core magnetometer, a double core sensor comprises two mutually parallel cores each provided with a primary and a secondary winding. The former are opposed, the latter are connected in series. The primary winding is supplied with a constant current by means of a low frequency transmitter (v=50 to 1000 Hz). The current intensity is sufficient to magnetise the highly permeable cores to saturation. A voltage is induced in the secondary windings by the changing magnetic field of the primary coils.

With no external magnetic field, the primary fields in the two cores are equal and opposite. Similarly, in the two secondary coils during the time in which the magnetic flux density B changes, equal and opposite voltages are induced, which add up to zero. In the presence of an external field component $H_0$ parallel to the longitudinal axis of the cores, this symmetry shifts by the value of $H_0$. The operating point on the B(H) curve is shifted, and the induced impulses no longer add up to zero, since with a change of H in one core, saturation is achieved faster than in the other. The result is that the voltage pulses of the derivative with time of the flux density dB/dt appear in the two cores at different times. The sum $dB_1/dt+dB_2/dt$ goes from zero to different signals, the breadth and distance apart in time of which are dependent on the amplitude of the external magnetic field $H_0$ and serve to determine the size of $H_0$.

An example of a commercial sensor which operates using the principle described above is the MAG-03 MS-sensor from Bartington Instruments Ltd.

With such magnetic field sensors, an accuracy of about 5 nT can be achieved in the measurement range B<1 mT. Thus it is possible to determine the magnetic field $B_d$ with such sensors.

In order to be able to determine the polarisation- dependent magnetic field $B_d$ of polarised gas in the presence of an applied field $B_0$ (e.g. the ambient field or a substantially uniform generated magnetic field within a transporter device), the polarisation-dependent magnetic field is advantageously determined by displacing the measuring apparatus and container (gas storage cell) relative to each other. This is advantageously achieved in that in a first position as close as possible to the wall of the container containing the nuclear spin polarised gas, a magnetic field sensor is used to record the field value, constituted by the field of the applied field $B_0$ and the field of the nuclear spin polarised gases in the container ($B_d$ at the equatorial plane of the container). After recording this signal the container is moved relative to the sensor to a position distanced from the sensor, preferably in the direction of the axial-applied field, by at least five times the radius of the container. The field component caused by the nuclear spin polarised gas then falls to less than 1% of its original value. This means than in this position only the value of the applied field $B_0$ is measured. The difference between these two signals can be used to determine the value of $B_d$ and thus the degree of polarisation P can be determined using equation (2) given above. It is clearly possible to increase the accuracy of the results obtained for the degree of polarisation using this method by making a series of measurements. In a further embodiment, the magnetic field sensor is displaced from the container. If the applied field $B_0$ changes on displacing the sensor, this must be taken into consideration when calculating the degree of polarization. Moreover if measurement is not made in the equatorial plane of the container, this too must be taken into consideration. Thus if the field is measured in the polar direction of the container, the difference is $B_d'=2\times B_d$.

These two methods have the advantage that commercially available magnetic field sensors can be used even by inexperienced personnel to determine the magnetic field of the nuclear spin polarised gases to an accuracy of 10%, advantageously 2%. With regard to geometric uncertainties, polarisation determination to 50%, advantageously to <10%, is quite possible.

In a second embodiment of the method of the invention $B_d$, and hence P, may be determined by using a high frequency magnetic pulse to reverse the polarisation and by measuring the resulting magnetic field change $\Delta B$ without moving the sensor and the container (the gas storage cell) relative to each other.

In this method, the polarisation-dependent magnetic field is advantageously determined by applying a high frequency magnetic pulse over the applied field, so that the sign of P is reversed by nuclear magnetic resonance. To this end, suitable coils or a solenoid are used to emit a high frequency magnetic field pulse of varying amplitude and frequency $$B(t)=B_1(t).\cos(\omega(t).t) \qquad (3)$$

perpendicular to the applied field $B_0$.

This magnetic field change based on the sign reversal of P preferably occurs on the principle of "fast adiabatic passage", fully described in A. Abragam, "The Principles of Nuclear Magnetism", Oxford University Press, London, England, 1973 (see especially pages 34–36 and 65–66). In this method, the frequency $\omega(t)$ of the high frequency magnetic field pulse during the pulse period is pushed beyond the resonance frequency of the nuclear dipole moment:

$$\omega_0 = \frac{2\pi\mu_N}{hI_N} \cdot B_0 \qquad (4)$$

where h is Planck's constant, and $I_N$ is the nuclear spin quantum number. If the pulse period is short and the high frequency field strength $B_d$ (t) is chosen correctly, the polarisation is completely reversed with no reduction in magnitude. This means that the reading of the magnetic field sensor changes by an amount $$\Delta B=2B_d \qquad (5)$$

In comparison with the method described above, in which the sensor and container are displaced with respect to each other, the method in which the field $B_d$ is determined using a magnetic field pulse has the advantage that a measuring signal $\Delta B=2B_d$ which is twice as large is obtained.

A complete reversal is obtained using the principle of "fast adiabatic passage" (see Abragam (supra)) if the following conditions are satisfied as regards emitting a high frequency pulse from a magnetic field pulse transmitter:

1. The applied high frequency magnetic field strength $B_1$ must be large in comparison with the magnetic field variation $\Delta B_0$ which the applied field $B_0$ exhibits because of inhomogeneities in the container dimensions.
2. The frequency shift $\Delta\omega$ between the start and end of the high frequency pulse must be large compared with the broadening of the nuclear resonance lines caused by the field variation $\Delta B_0$.
3. The pulse duration $\Delta t$ must be short compared with the characteristic transverse relaxation time $T_2$ of the gas.
4. The product $B_1 \cdot \Delta t$ must be large compared with $hI_N/(2\Pi\mu_N)$.

This polarisation reversal method is particularly suitable as a complete polarisation reversal can also be achieved in an extensive gas volume, although the applied field $B_0$ for maintaining the polarisation can vary slightly spatially by $\Delta B_0$. The method is thus robust and guarantees reproducible results, even when the nuclear spin polarised gas container is changed or, for example, external stray fields are superimposed, as may be the case in different locations. The method can advantageously be used in transportable magnetic fields to determine the polarisation of a gas on site even by inexperienced personnel.

A further method of producing a polarisation reversal is to apply a magnetic pulse using the principle of the 180° nuclear resonance pulse or "Πpulse", as fully described in A. Abragam (supra) pages 32–34.

In this method, suitable coils or a solenoid are used to produce a high frequency magnetic field pulse of varying amplitude and frequency (equation (3)) perpendicular to the applied field.

For a complete reversal of the nuclear spin polarisation of the gas using the n pulse principle, a magnetic field pulse with frequency $\omega_0$ (equation (4)) must be applied by a magnetic field pulse transmitter using the following conditions:

1. The applied high frequency magnetic field strength $B_1$ must be large in comparison with the magnetic field variation $\Delta B_0$ which the applied field $B_0$ exhibits because of inhomogeneities in the container dimensions.
2. The pulse duration $\Delta t$ must be short compared with the characteristic transverse relaxation time $T_2$ of the gas.
3. The relationship $$j \cdot \pi = \frac{2\pi\mu_N}{hI_N} \cdot B_1 \cdot \Delta t \qquad (6)$$

must be satisfied, where h is Planck's constant and $I_N$ is the nuclear spin quantum number, $\mu_N$ is the nuclear dipole moment of the isotope under consideration, and j=1,3,5,7, etc, however j=1 is normally selected.

In contrast to the "fast adiabatic passage" method, in the n pulse method the relationship (6) must hold exactly. This is rendered more difficult if variations $\Delta B_0$ occur in the applied field $B_0$ over the gas volume.

For larger gas volumes, as considered in the present invention, significant field variations $\Delta B_0$ occur over the gas volume so the more robust "fast adiabatic passage" method with the particular advantage of complete reversal of the nuclear spin polarisation of the gas is preferred. This does not, however, constitute a limitation of the inventive concept of measuring a polarisation reversal with a magnetic measuring apparatus using nuclear resonance methods.

Viewed from a further aspect, the present invention also provides apparatus for determining the magnetic field ($B_d$) of a nuclear spin polarised gas (and preferably also for determining the degree of polarisation P thereof), said apparatus comprising a magnetic field sensor arranged to determine the magnetic field at at least two positions relative to a container containing a nuclear spin polarised gas, optionally magnetic field applying means arranged to apply a magnetic field to said container, and optionally computing means for determining the degree of polarisation of the polarised gas from the magnetic fields determined by the sensor.

In this apparatus, the sensor may operate to determine the magnetic fields at the various relative positions or it may simply determine the field difference between the positions.

In the apparatus, the sensor may be movable relative to the container or alternatively it may comprise separate sensors located at different positions relative to the container. The different positions will generally include positions relative closer to and further away from the container. The relative motion of sensor and container may be achieved by moving sensor and/or container to preset receiving sites or along a guide, e.g. using a drive means (for example a motor-driven or hand operated drive means)

In this apparatus, the means for applying a magnetic field are preferably means, e.g. a permanent or electromagnet, for applying a substantially uniform field $B_o$.

Viewed from an alternative aspect the invention also provides apparatus for determining the magnetic field ($B_d$) of a nuclear spin polarised gas (and preferably also for determining the degree of polarisation (P) of the gas), said apparatus comprising a magnetic field sensor and means for applying a time variant magnetic field to a container containing a nuclear spin polarised gas, optionally also means for applying a substantially uniform magnetic field to said container, and optionally computing means for determining the degree of polarisation of the polarised gas from the magnetic field variation determined by the sensor.

In this second form of apparatus according to the invention, there may if desired be two or more sensors and the sensor and container may be movable relative to each other.

In both forms of the apparatus of the invention the container is preferably spherical and the sensors are preferably highly sensitive, e.g. SQUIDs or Forster principle magnetometers.

The first apparatus of the invention thus conveniently comprises apparatus for determining the degree of polarisation (P) of nuclear spin polarised gases in which the nuclear spin polarised gas is placed in a container, the apparatus comprising: at least one highly sensitive magnetic field sensor, wherein the sensor and the container are arranged so as to be displaceable relative to each other, so that the magnetic field can be determined in at least two locations, e.g. one close to and one distanced from the container, and thus the magnetic field $B_d$ can be determined.

The second apparatus of the invention also conveniently comprises apparatus for determining the degree of polarisation (P) of nuclear spin polarised gases in which the nuclear spin polarised gas is placed in a container, the apparatus comprising: at least one highly sensitive magnetic field sensor, and a high frequency magnetic field pulse transmitter arranged to emit a high frequency magnetic field pulse of variable amplitude and frequency.

The apparatus of the invention is desirably incorporated into apparatus for transporting hyperpolarised gases in which the container is placed within an area of highly uniform applied magnetic field in a chamber within the transporter apparatus.

In a special embodiment, the high frequency magnetic field pulse transmitter comprises coils or solenoids. In one particular embodiment, the magnetic field pulse transmitter is constructed so that a magnetic field pulse is emitted by which the polarisation is completely reversed with no reduction in magnitude.

The use of the apparatus and method of the invention are particularly advantageous with respect to the prior art for the following reasons:

Commercially available apparatus components (e.g. sensors) with high precision and with reproducible results with a relative error of only 0.5% or less can be used. These commercially available apparatus components are calibrated so expensive calibration can be avoided.

The prior art methods for determining the nuclear spin polarisation which induce small nuclear resonance excitations are based on recording the dynamic nuclear spin resonance signal thus produced, recorded with a receiver apparatus. A very costly calibration is necessary for absolute polarisation determination, in which very small resonance signals are measured, which are very sensitive to disturbances from external influences such as container geometry or the construction of the receiver apparatus. In order to produce good results, each receiver apparatus must be separately calibrated, and that calibration is only valid for one container geometry. Using a magnetic field sensor as in the invention means that the very expensive calibration of the receiver apparatus and standardisation of the container geometry is no longer required. The influence of container geometry can be readily calculated. The static magnetic field of the nuclear spin polarised gas is measured. Then a series of measurements of the static magnetic field before and after polarisation reversal can be made to substantially increase the accuracy of the method. The measuring method can thus advantageously be embodied in a measuring apparatus. The measuring apparatus itself is highly reproducible and reliable. In particular, the measuring method is also suitable for use by inexperienced personnel because of its robustness.

Figure 2:
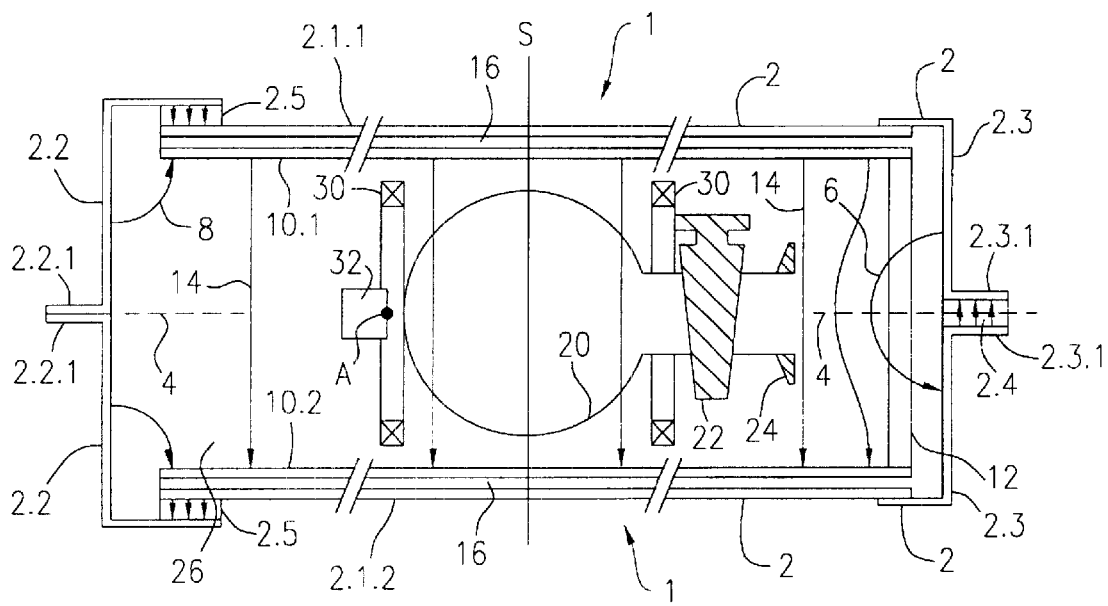
Figure 3:
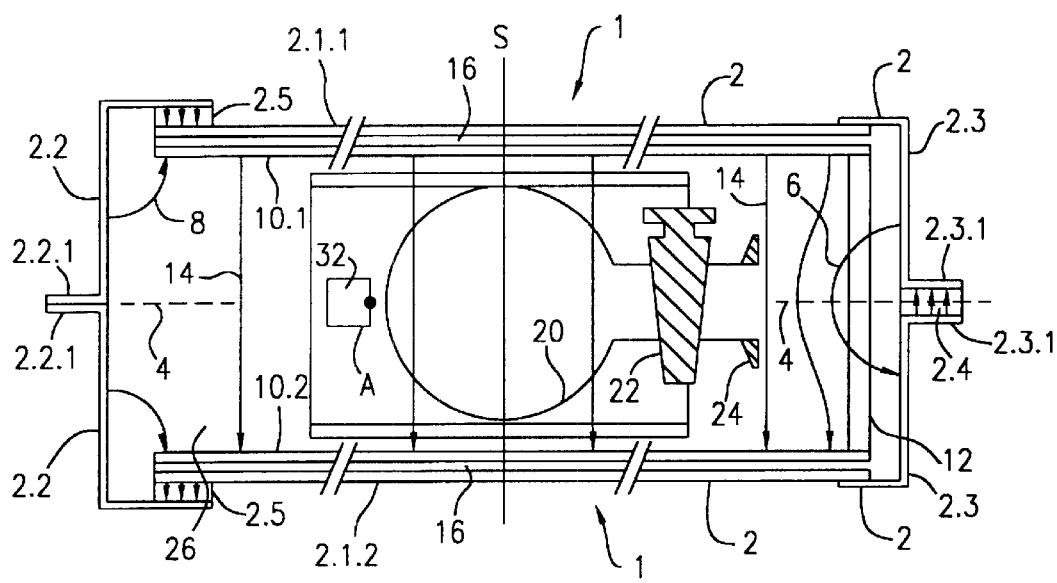
Figure 4:
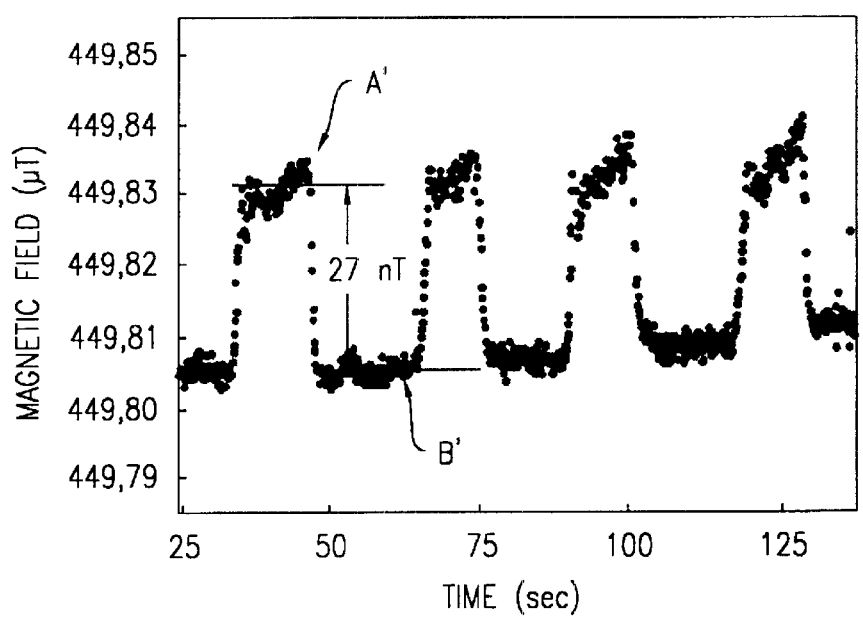
Figure 5:
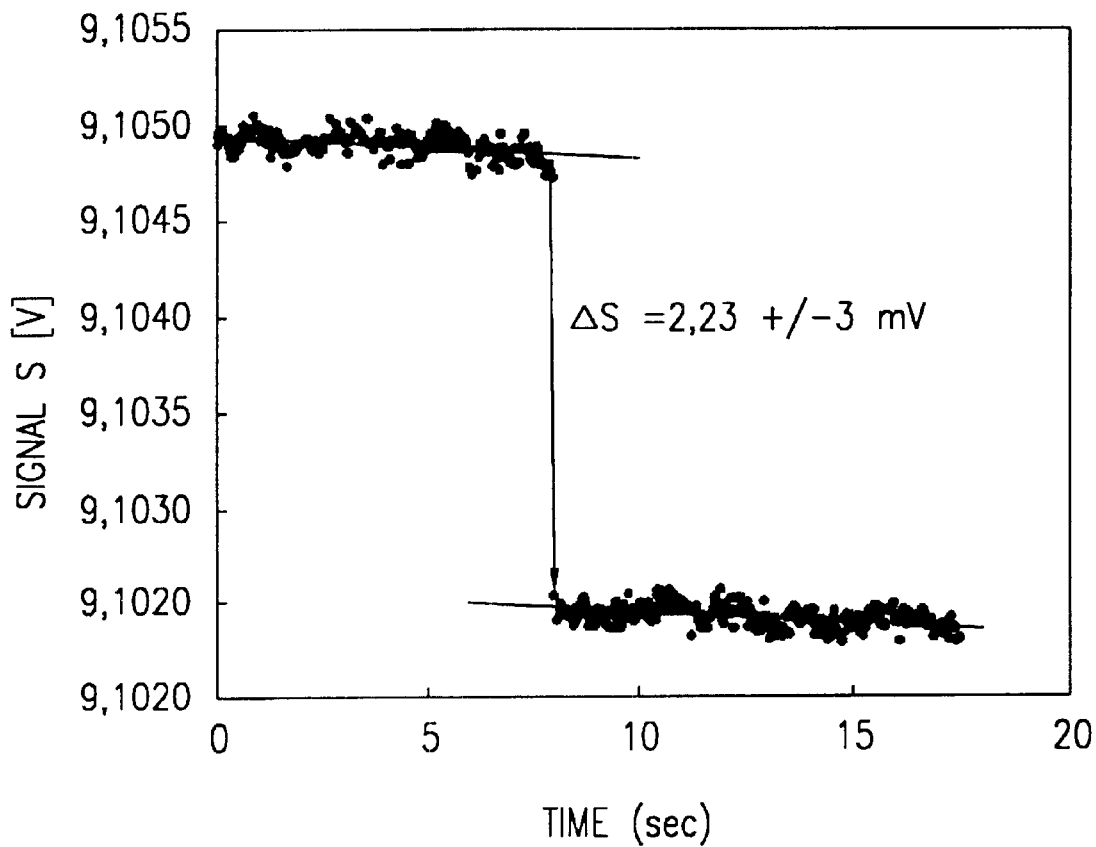

Embodiments of the invention will now be described with reference to the accompanying drawings, which are provided by way of illustration and are in no way limiting and in which:

FIG. 1: shows a perspective external view of a transport apparatus for hyperpolarised gas;

FIG. 2: shows a cross section through a transport apparatus comprising a magnet (a pot magnet), and a storage cell for nuclear spin polarised gases arranged inside;

FIG. 3: shows a section through a further embodiment of the apparatus of the invention;

FIG. 4: shows the determined magnetic field using a first apparatus according to the invention in which the container is placed on the magnetic field sensor or distanced from the sensor; and FIG. 5: shows the determined magnetic field using a second apparatus according to the invention using the "fast adiabatic passage" method.

Referring to FIG. 1 there is shown a perspective external view of an embodiment of a transport apparatus, formed as a two-part cylinder-shaped pot magnet 1 with an upper portion 1.1 and a lower portion 1.2. The Figure also shows the axis of rotational symmetry S of the pot magnet and the magnetic field lines of external magnetic fields, for example the earth's magnetic field. It particularly shows the transverse component of an external magnetic field or stray field $B_s^\perp$, which does not penetrate inside the pot magnet, but because of the small magnetic resistance of the yoke 2 (which is preferably formed from soft iron) is directed around the internal space. The stray field component $B_s^{//}$, which is parallel to internal field $B_o$, is perpendicular to the yoke base and is homogenised by $\mu$-metal or soft iron pole pieces located internally of yoke 2 and hence contributes to $B_0$ without affecting its homogeneity.

FIG. 2 shows an axial cross section through the transport apparatus of FIG. 1, useful in particular for transporting nuclear spin polarised $^3$He or $^{129}$Xe, especially $^3$He. The apparatus comprises a pot magnet apparatus with a container for the nuclear spin polarised gas located within it. Using this transport apparatus the gas exhibits an extremely long wall depolarisation relaxation time.

The pot magnet 1 comprises a box-shaped yoke 2, preferably formed from soft iron to repel the magnetic flux and to protect from external fields. The box-shaped yoke 2 also comprises two yoke bases as middle portion 2.1. The yoke bases 2.1 in this case may for example comprise two circular (or polygonal) disks 2.1.1 and 2.1.2. At the edge of the yoke bases, circumferential closed strips 2.2 and 2.3 are arranged to form a casing. These are different in the embodiments shown in the left and right halves of FIG. 2. The circumferential strips 2.2 or 2.3 are arranged on both the upper disk 2.1.1 and the lower disk 2.1.2, giving the pot magnet an upper and a lower portion, which in the embodiment illustrated on the left press together in the middle plane of the magnet apparatus at the bent flanges 2.2.1. In the second embodiment shown on the right, the flanges 2.3.1 are at a distance apart, to form an opening for field sources 2.4, for example permanent magnets, in the middle plane of pot magnet 1. The field line gradient resulting from positioning the field source, for example a permanent magnet, in the middle between the upper and lower edge of the pot magnet is shown at 6. In the first embodiment shown on the left, the height of the two yoke casing halves 2.2 is greater than the distance apart of yoke bases 2.1.1, 2.1.2. In the gap between casing and base, it is possible to arrange field sources in a facing position 2.5. The field line gradient at the edge region resulting from this arrangement is shown at 8.

The two opposed pole shoes 10.1 and 10.2 are responsible for the homogeneous field within the pot magnet. The pole shoes are formed from parallel, opposed, magnetic field homogenising plates, e.g. of $\mu$-metal or soft iron in the embodiment shown. $\mu$-metal is a material with a very high homogenising power for an external magnetic field, for example a stray magnetic field $B_s^{//}$, and is characterized by a very small remanence.

In the present embodiment, $\mu$-metal A from Vacuumschmelze, Postfach 2253, 63412 Hanau, Germany, was used which had the following properties:

| | | |
|---|---|---|
| Stat. Coercive field strength | $H_c$ | $\leq 30$ mA/cm |
| Permeability | $\mu_{(4)}$ | $\geq 30000$ |
| Maximum permeability | $\mu_{max}$ | $\geq 70000$ |
| Saturation induction | $B_S$ | $\geq 0.65$ T |

Other materials however can be used.

The pole shoes are desirably kept in opposed parallel relationship by three or more spacers in or by circular or polygonal spacer rings. As illustrated in FIG. 2, the distance between the μ-metal plates is ensured by three spacers 12, only one of which is shown.

The resulting homogeneous magnetic field between the pole shoes 10.1 and 10.2 of μ-metal is shown at 14 in the present embodiment. As can be seen from the embodiment shown in FIG. 1, a particularly homogeneous magnetic field is produced inside the pot magnet due to the homogenising power of the μ-metal, independent of external fields, while in the edge regions, depending on the arrangement of the field sources, a deviating field gradient 6 or 8 is produced. If the field sources are only arranged in the middle plane 4, as shown in the right hand side of pot magnet 1, a substantial portion of the magnetic flux extends outside the casing because of the small magnetic resistance and passes through more strongly from the edge into the field between the pole shoes. The field thus falls substantially from the edge inwards and the desired homogeneity is destroyed even at a relatively small distance between the two pole pieces. By arranging the permanent magnets in a facing position on the pot bases, as shown in FIG. 2 for the left hand region of the magnet, the field drops off substantially between the pole shoes 10.1, 10.2 as shown by field line 8, because the casing close to the pole shoes pulls on the edge field and weakens it.

The very homogeneous field 14, produced in the space between the pole shoes because of the extremely high permeability of the μ-metal or soft iron plates used as pole shoes 10.1, 10.2, can be further strengthened by inserting a magnetic resistor 16 between pole shoes 10.1, 10.2, and the yoke 2.1.1 or 2.1.2. Preferably, a deformation-resistant, non-magnetic plate, for example a plastic plate 16, or, to save weight, a honeycomb structure, is used. Plate 16 can be glued to pole shoes 10.1, 10.2 and thus ensures that the pole shoes 10.1, 10.2 are flat and parallel.

The container (storage cell) 20 for the polarised gas is in the central middle portion of the magnetic field containing chamber 26 in pot magnet 1 between the two pole shoes 10,1, 10.2. Container 20 is preferably formed from iron-free glass and has, for example, an iron concentration of less than 20 ppm. Advantageously, the container is so constructed that it also constitutes a high barrier to helium diffusion. In this way, wall relaxation times of more than 70 hours are achieved. Storage cell 20 can be pumped out before use and as is normal in high vacuum technology, it can be heated to remove the remaining layers of water. This measure is of advantage in the present invention but not necessary. The storage cells are closed, for example, using a normal glass tap 22 and are connected to a filling point for polarised gas via a glass flange 24.

In order to determine the degree of polarisation, in accordance with the invention, an apparatus for determining the degree of polarisation is provided inside the transport apparatus.

In a first embodiment of the invention, only one magnetic field sensor 32 is arranged in the transport container, e.g. a sensor which operates using the Förster principle and, for example, obtains its measuring signal by saturation of a highly permeable transformer core by the external field. A commercially available example of such a magnetic field sensor is the MAG-03 MS sensor from Bartington Instruments Ltd, with which a measuring range B<1 mT can be obtained, for example with an accuracy of about 5 nT.

When the magnetic field $B_d$ produced by nuclear spin polarisation is to be determined using such an arrangement, then the magnetic field is first determined using the magnetic field sensor initially in position A as shown near to the cell. In this position, the magnetic field is constituted by the value of the applied field $B_0$ plus the value of the nuclear field $B_d$ formed by the nuclear spin polarisation. The cell must then be displaced relative to the magnetic field sensor. This can be effected by moving the cell in the direction of the axial applied field by at least five times its radius or by moving the magnetic field sensor by this value. Once in position, the field at such a distance from the storage cell for the polarised gas will only reflect the applied field $B_o$. The difference between the two values enables $B_d$ to be determined using equation (2).

In order to further increase the accuracy of the measurements, a further embodiment can be used, in which in addition to the magnetic field sensor a magnetic field pulse transmitter is provided, for example that shown in FIG. 2 as a HF-coil pair 30, with which a high frequency magnetic field pulse of varying amplitude and frequency (Equation (3)) perpendicular to the applied field $B_0$ can be produced. By appropriate choice of the high frequency magnetic field pulse, it is possible using the "fast adiabatic passage" method to produce a complete reversal of the nuclear spin polarisation in an external applied field. The static dipole field before $(B_0+B_d)$ and after $(B_0-B_d)$ the polarisation reversal is then measured using the highly accurate magnetic field sensor 32. In this way, a signal $2B_d$ is obtained to give the dipole field produced by the nuclear spin polarisation directly from such a measurement.

The conditions for adiabatic fast passage require a relatively homogeneous magnetic field such as the applied field. The applied field $B_0$ described for the transport apparatus satisfies these conditions.

FIG. 3 shows an alternative embodiment of the invention, in which the magnetic field pulse transmitter uses a solenoid 300 instead of HF coils.

FIG. 4 shows the magnetic field measured as a function of time for a container of nuclear spin polarised $^3$He gas obtained by placing the container on the magnetic field sensor and then distancing it from the sensor. In this example, a spherical container with a diameter of 5.5 cm was filled with 2.68 bar of $^3$He (at 295 Kelvin) and displaced in an apparatus such as that of FIG. 2. A' is the measured field adjacent the container and B' is the field measured remote from the container, ie. essentially the field $B_o$. The step-shaped trace clearly shows the applied field $B_0$ of 449.805 μT adding to the hyperpolarised magnetic field $B_d'$ of 27 nT.

The field measured in non-limiting fashion in the pole position of the container of $B_d'=2.B_d$. This enabled a polarisation of 29% to be calculated. This example is solely by way of illustration and in no way limits the inventive concept.

FIG. 5 shows the magnetic field measured as a function of time for a container of hyperpolarised $^3$He using polarisation reversal by "fast adiabatic passage". It shows the voltage signal of the magnetic field measuring apparatus. At time t=8 s, polarisation reversal occurs, as is clearly shown by the jump in the points during a series of measurements. Following the development with time of the external magnetic field at the sensor location before and after the polarisation reversal advantageously enables systematic variations which are independent of the nuclear spin polarisation of the gas to be detected. Such variations can, for example, be due to changes in the earth's magnetic field, perhaps by moving magnetic materials. While dynamic nuclear resonance signals can be perturbed by such, the determination of static magnetic fields of nuclear spin polarised gas using a series of measurements is robust.

The present apparatus and method allow a measurement of nuclear spin polarisation which requires no costly calibration and does not use a dynamic nuclear resonance signal to determine $B_d$, but directly measures the static dipole field of the polarised gas. Problematic calibration of dynamic nuclear resonance signals can thus be avoided. The methods presented here for measuring the degree of polarisation, in particular using the fast adiabatic passage method, enable-even a non skilled person to readily determine the degree of nuclear spin polarisation.

What is claimed is:

1. A method of determining the degree of polarisation of a nuclear spin polarised gas in a container comprising displacing said container and a magnetic field sensor relative to each other, measuring said magnetic field before and after movement of the container and the magnetic field sensor to obtain measurable magnetic field signals, detecting the magnetic field $B_d$ as a function of the difference between the measurable magnetic field signals, and determining the degree of polarisation of the gases from the detected magnetic field $B_d$.

2. A method of determining the degree of polarisation of a nuclear spin polarised gas in a container, comprising applying a high frequency magnetic field pulse to the gas to reverse the polarisation of the gas, measuring the magnetic field before and after application of the high-frequency magnetic field pulse to obtain measurable magnetic field signals, detecting the magnetic field $B_d$ such that the difference between the measurable magnetic field signals is twice the value of the magnetic field $B_d$, and determining the degree of polarisation of the polarised gas from the detected measurable magnetic field $B_d$.

3. The method as claimed in claim 1 wherein the calculation of the degree of polarisation of the polarised gas is dependent on the density of the polarised gas and a geometry factor dependent on the shape and size of the container.

4. The method as claimed in claim 2 wherein the calculation of the degree of polarisation of the polarised gas is dependent on the density of the polarised gas and a geometry factor dependent on the shape and size of the container.

5. The method as claimed in claim 1 wherein the container is spherical.

6. The method as claimed in claim 2 wherein the container is spherical.

7. The method as claimed in claim 1 wherein the polarized gas is selected from the group consisting of $^3$He, $^{129}$Xe and polarised gases containing $^{19}$F, $^{13}$C or $^{31}$P.

8. The method as claimed in claim 2 wherein the polarized gas is selected from the group consisting of $^3$He, $^{129}$Xe and polarised gases containing $^{19}$F, $^{13}$C or $^{31}$p.

9. The method as claimed in claim 1 wherein the magnetic field sensor has a measurement accuracy of 5 nT and is capable of determining $B_d$ with an accuracy of within 50%.

10. The method as claimed in claim 1 wherein the magnetic field sensor has a measurement accuracy of 5 nT and is capable of determining the magnetic field $B_d$ with an accuracy of within 50%.

11. The method as claimed in claim 1 wherein the sensor has a measurement accuracy of 5nT and is capable of determining the magnetic field $B_d$ with an accuracy of within 10%.

12. The method as claimed in claim 2 wherein the magnetic field sensor has a measurement accuracy of 5 nT and is capable of determining the magnetic field $B_d$ with an accuracy of within 10%.

13. The method as claimed in claim 1 wherein the container is placed in a substantially uniform applied magnetic field $B_o$.

14. The method as claimed in claim 2 wherein the container is placed in a substantially uniform applied magnetic field $B_o$.

15. The method as claimed in claim 1 wherein said container and said magnetic field sensor are within a magnetized gas transport apparatus.

16. The method as claimed in claim 2 wherein said container and said magnetic field sensor are within a magnetized gas transport apparatus.

17. The method as claimed in claim 2 wherein the polarisation reversal is obtained by a fast adiabatic passage.

18. The method as claimed in claim 2 wherein the high frequency magnetic field pulse is a 180° or Π nuclear resonance pulse.

19. Apparatus for determining the degree of polarisation of a nuclear spin polarised gas comprising a magnetic field sensor and a container containing a nuclear spin polarised gas, said magnetic field sensor and container being displaceable relative to each other so that the magnetic field can be determined in at least two locations, and magnetic field applying means arranged to apply a magnetic field to the container.

20. The apparatus of claim 19 further comprising computing means to determine the degree of polarisation of the polarised gas from the magnetic fields determined for the at least two locations by the magnetic field sensor.

21. Apparatus for determining the degree of polarisation of a nuclear spin polarised gas comprising a magnetic field sensor a container containing a nuclear spin polarised gas, and a high frequency magnetic field pulse transmitter arranged to apply a time variant, magnetic field to said container which reverses the polarisation of said gas.

22. The apparatus of claim 21 further comprising means for applying a substantially uniform magnetic field to said container.

23. The apparatus of claim 21 further comprising means for determining the degree of polarisation of the polarised gas from the time variant magnetic field applied to the container as measured by the magnetic field sensor.

24. The apparatus as claimed in claim 23 wherein the high frequency magnetic pulse transmitter comprises at least one coil.

25. The apparatus as claimed in claim 21 wherein said container is spherical.

26. The apparatus as claimed in claim 21 in the form of a transport apparatus wherein said container and magnetic field sensor are enclosed in a magnetic field chamber.

* * * * *

UNITED STATES PATENT AND TRADEMARK OFFICE
CERTIFICATE OF CORRECTION

PATENT NO. : 6,486,666 B1
DATED : November 26, 2002
INVENTOR(S) : Tino Grossmann et al.

It is certified that error appears in the above-identified patent and that said Letters Patent is hereby corrected as shown below:

<u>Title page,</u>
Item [73], cancel in its entirety;
Item [57], ABSTRACT,
Line 5, cancel "pola gas" and insert -- polarized gas --;

<u>Column 1,</u>
Line 10, cancel "3He" and insert -- $^3$He --;
Line 46, cancel "P>1x10$^{-2}$" and insert -- P≥1x10$^{-2}$ --;

<u>Column 3,</u>
Line 18, cancel "Forster" and insert -- Förster --;

<u>Column 4,</u>
Line 8, cancel "This means than in this position" and insert -- This means that in this position --;
Line 60, cancel "field strength B$_d$(t)" and insert -- field strength B$_1$ (t) --;

<u>Column 5,</u>
Line 18, cancel "relaxation time T$_2$" and insert -- relaxation time T$_2$* --;
Line 41, cancel "using the n pulse principle" and insert -- using the π pulse principle --;
Line 63, cancel "n pulse method" and insert -- π pulse method --; and <u>Column 8,</u>
Line 3, cancel "$^{31}$p" and insert -- $^{31}$P --.

Signed and Sealed this

Eighth Day of April, 2003

JAMES E. ROGAN
*Director of the United States Patent and Trademark Office*